(12) United States Patent
Lindahl (10) Patent No.: US 6,282,727 B1
(45) Date of Patent: Sep. 4, 2001

(54) SPORTS EYE WEAR WITH DETACHABLE GOGGLE MEMBERS

(76) Inventor: Arthur Charles Lindahl, 242 Glen Ellen Dr., Ventura, CA (US) 93003

( * ) Notice: Subject to any disclaimer, the term of this patent is extended or adjusted under 35 U.S.C. 154(b) by 0 days.

(21) Appl. No.: 09/352,898

(22) Filed: Jul. 13, 1999

(51) Int. Cl.$^7$ .................................................. A61F 9/02
(52) U.S. Cl. ........................................ 2/428; 2/431; 2/436
(58) Field of Search ................................ 2/431, 436, 437, 2/439, 428, 430, 440, 441, 442, 8, 9, 10, 424; 351/158

(56) References Cited

U.S. PATENT DOCUMENTS

| | | |
|---|---|---|
| D. 339,365 | 9/1993 | Bollé . |
| 1,853,872 * | 4/1932 | Meyrowitz ............................... 2/440 |
| 2,918,676 * | 12/1959 | Matheson ................................. 2/440 |
| 3,233,249 | 2/1966 | Baratelli et al. . |
| 3,233,250 | 2/1966 | Johassen . |
| 4,070,103 | 1/1978 | Meeker . |
| 4,176,410 | 12/1979 | Matthias . |
| 4,405,212 | 9/1983 | Cooper . |
| 4,447,914 | 5/1984 | Jannard . |
| 4,515,488 | 5/1985 | Tackles . |
| 4,571,748 * | 2/1986 | Carroll et al. ............................ 2/436 |
| 4,674,851 | 6/1987 | Jannard . |
| 4,730,915 | 3/1988 | Jannard . |
| 4,779,291 | 10/1988 | Russell . |
| 4,822,161 | 4/1989 | Jimmy . |
| 4,824,233 | 4/1989 | Jannard . |
| 4,859,048 | 8/1989 | Jannard . |
| 4,867,550 | 9/1989 | Jannard . |
| 4,868,930 | 9/1989 | Blackstone . |
| 4,934,807 | 6/1990 | Bollé . |
| 5,033,128 | 7/1991 | Torres . |
| 5,054,903 | 10/1991 | Jannard . |
| 5,056,163 | 10/1991 | Chou . |
| 5,093,940 | 3/1992 | Nishiyama . |
| 5,098,180 | 3/1992 | Toby . |
| 5,138,723 * | 8/1992 | Bolle ........................................ 2/439 |
| 5,191,364 | 3/1993 | Kopfer . |
| 5,243,711 | 9/1993 | Graham . |
| 5,339,119 | 8/1994 | Gardner . |
| 5,371,554 | 12/1994 | Aspesi . |
| 5,412,438 | 5/1995 | Bollé . |
| 5,617,588 * | 4/1997 | Canavan et al. ..................... 2/441 X |
| 5,894,606 * | 4/1999 | Chiang ..................................... 2/440 |
| 6,052,828 * | 4/2000 | Widdemer ............................. 2/161.2 |
| 6,062,688 | 5/2000 | Vinas . |
| 6,094,751 * | 8/2000 | Parks ........................................ 2/431 |
| 6,139,144 | 10/2000 | Hynansky . |

* cited by examiner

*Primary Examiner*—Peter Nerbun
(74) *Attorney, Agent, or Firm*—Curtis L. Harrington (57) ABSTRACT

Eye wear includes at least a single piece lens supported and captured within a frame. In one embodiment a ramped protrusion from the lens engages a matching accommodating slot and lies off of a main slot in the frame which engages the upper edge of the lens. A lower lens is engaged by a fitted member having a soft sealing structure extending to one side. The fitted member is contoured to and attaches adjacent the edge of the lens and may extend from a point near the outermost edge of one side of the eye wear and to the nose area. Another embodiment of the fitted member is available as a continuous length having notches and which may be conformed to a wide variety of lens shapes. Another length of fitted member can also serve as a nose support structure extending completely across the front lens of the eye wear. Embodiments of the invention are utilizable with conventional spectacles. All embodiments contemplate removabilty, replaceability and interchangeability.

24 Claims, 8 Drawing Sheets

SPORTS EYE WEAR WITH DETACHABLE GOGGLE MEMBERS

FIELD OF THE INVENTION

The present invention relates to the field of sports & safety eye wear and more specifically to eye wear having improved lens retention and members which may be added to the bottom edge of eye wear lens members to form an improved goggle structure.

BACKGROUND OF THE INVENTION

Conventional sports & safety eye wear currently exist which allow the user a wide angle of view. This type of eye wear is typified by a singular or two lenses which extends from the outside of one of the wearer's eyes and extends across to the outside of the other of the wearer's eyes, and only partially interrupted by the structures which support the eye wear at the bridge of the nose. This is a partial interruption since the support structures are typically supported only by the center of the singular lens, which is in turn supported by the upper portion of the frame. The support structure extends inside the singular lens to garner support from the user's nose, and the singular lens is kept outward and generally downward opening downward and lower on the user's face. Thus the wide view afforded by the singular lens comes at the expense of having a wide open space between the lower edge of the lens and the user's face. The same issues occur in two lens eye wear in the wide open space between the lens & user's face.

Goggles hug and seal with the face of the user to isolate the eyes as much as possible from wind and debris. The sealing can occur around each eye, and the protected area most often includes the bridge of the nose. Even where the enclosure extends across the area adjacent both eyes, goggles still generally restrict the view of the user. The restriction usually comes with the support structure which is used to seal against the face and closely adjacent to the eyes, and typically surrounds the entire lens fully.

In terms of usage, a user is faced with having to buy both goggles and conventional sports glasses, and to use the appropriate eye wear depending upon circumstances. Where debris is severe enough, goggles are worn at the sacrifice of an expanded viewing angle, more heavily structured and bulky. Where conventional open sports eye wear are worn, the user suffers the debris, particularly wind and dust, which may enter the eyes behind the lenses. In addition, conventional sports eye wear, by having a significant gap on the face, even where the gap between the bottom of the lens and the face surrounding the eyes is low on the face, admits significant amounts of light. Where the user gazes down, there will be a sudden change in light levels, which can both annoy the user and stress the user's eyes. The effect is most pronounced where the lens is particularly dark.

Another aspect of eye wear not served well by goggles includes the ability for comfort and ventilation. A good seal is usually achieved at the expense of ventilation and with significant pressure on the face surrounding the eyes. In some cases specialized ventilation ports are formed in the side walls of the lens support structures, but they are not always located properly or structured to provide adequate ventilation. Even where adequate ventilation is provided, the goggles do not provide a comfortable fit.

Goggle framing is usually fairly durable and allows for a long useage life. The seal used in conventional goggles is less able to withstand vigorous use, and tends to break down over a relatively short period of time. The seal break down usually occurs far short of the full use life of the overall goggle. Therefore, the ability to interchange goggle seals is important in extending the life of a goggle.

What is therefore needed is a new and improved sports eye wear structure including at least one lens member that may be held strongly in a frame and having structures which engage the lens member along the bottom edge, separate or in conjunction with a top and/or side edges, and which will permit a very gentle sealing with the face to inhibit wind and debris from entering the user's eyes and which will block unwanted light from the eyes. Further, to benefit interchange ability, the structures which forms the seal along the bottom portion of the lens or lenses should be removable so that a wearer can use the same eye wear in an open or closed format as the user wishes.

SUMMARY OF THE INVENTION

The eye wear includes a single piece lens or two lenses which may or may not be supported and captured within a frame using a ramped protrusion from the lens which engages a matching accommodating void and lies off of a main slot in the frame which engages the upper edge of the lens. Possible lenses include removable lenses, anti-fog lenses, as well as systems supplied as lens-only.

The lower lens is engaged by a fitted member having a sealing structure extending to one side. The side of the sealing structure extension which meets the face preferably has a smooth, non-porus surface to avoid collection of debris, body oil, although since the member is removable and easily washable, an open cell foam or other porus material, as well as a completely closed foam, non-externally porus material can be used as the sealing structure. The sealing structure which may have a finished end surface, would also be permissible. The sealing structure may operate in conjunction with a built-in or removable side shield and may accommodate a permanent or removable nosepiece.

The fitted member engaging the lower edge of the lens or lenses and which may extend from a point near the outermost edge of one side of the eye wear, or face and to the nose area. The end of the fitted member can be shaped to provide maximum accommodation of the nose support member and help seal in a manner complementary to the nose support member.

In another embodiment, the fitted member can extend from one side of the eye wear, completely through to the other side of the eye wear and form the structure which supports the lens against the nose. In both embodiments, the fitted member is intended to include the possibility of alteration by the user by cutting, trimming and the like to obtain maximum conformance to the particular shape of the user's eye wear.

The fitted member may include a plastic support piece having a generally U-shaped cross section for engaging the lower edge of the lens, and a small shelf, extending from the bottom portion of the U-shape which helps to support the sealing structure which seals against the face. Along the length of the shelf, a series of elongate rectangular ports assist in handling drainage of any sweat, or any rain or moisture which might have entered the eye shield area and collect along the bottom of the lens.

The plastic support piece will typically be extruded or injected and may be heat formed to a specific shape where it is desired to provide eye wear as a kit. Where the fitted member is provided as a retro-fit device for use with non-specific shapes of lenses, the fitted member will ideally have a series of angled slots along its length to permit bending conformance to a wide variety of shapes of lens edges without twisting or distorting the material. In another embodiment, shorter sections of material may be fitted along the lower edge of lens members. Attachment of any of the structures of the invention may be had by gluing, hooking or clipping, chemical bonding, welding, friction fit, screws, pressure, male and female pins and holes, attachment channel and groove, hook and loop members, magnets, suction, static attraction, melting or solvent, and independent attachment to other structures including any portion of the eye wear frame, temples, strap or lens. The structures of the invention may include homogeneous structures, or structures made of two or more different types of material. Materials which can be used include wood, metal, plastic, leather, cloth/fabric, foam, rubber, conforming material and any other material capable of making the seal now known or later discovered. Manufacture of the structures of the invention can occur by extrusion, injection, shaping, forming, molding or other manufacturing steps now know or later discovered.

BRIEF DESCRIPTION OF THE DRAWINGS

The invention, its configuration, and its construction will be further depicted in the following detailed description, taken in conjunction with the accompanying drawings in which.

DETAILED DESCRIPTION OF THE PREFERRED EMBODIMENT

The invention will be best described with reference to FIG. 1 which illustrates a perspective view of sports eye wear 11. Eye wear includes a curved frontal support 13, a pair of folding side temple supports 15 and which may be pivotally hinged to the frontal support 13. Here, a support strap 16 is shown engaging the ends of the temple supports 15.

Supported solely from the frontal support 13, a continuous lens 17 is suspended from the frontal support 13. The lens 17 has a right area 19 and a left area 21 separated by a nose area 23. The nose area 23 is the smallest vertical extent of the lens 17 and demarks some separation between the right and left areas 19 and 21 respectively. At and below the nose area 23 is a nose bridge support 25 which is attached to the lens 17. The nose bridge support 25 has a forward lens engaging portion 27 and a rearwardly extending nose bridge engagement portion 29. The support 25 is typically held in place by notches or other holding structure in the lens 17 which hold the support 25 in place.

Immediately below the right area 19 is a fitted member 31 having a fitted engagement piece 33 and a rearwardly extending sealing structure 35. The engagement piece 33 is typically made of a medium soft resilient plastic which can be slipped onto the bottom of the lens 17. A second fitted member 37 includes an engagement piece 39 and a sealing structure 41.

Engagement piece 33 follows the contour of the bottom edge (not seen where engaged) of the right area 19 of the lens 17. Here, the engagement piece 33 covers all of the bottom edge of the right area 19 and stops where the outer edge of the right area turns upward. The extent of engagement piece 33 need not stop here, but can continue upward if desired. At the rear of the curved frontal support 13, a continuous length of brow padding 43 may be provided. In such a configuration, the eye wear 11 is supported by a combination of the hugging action of the temple supports, the pressure of the frontal support 13 and brow padding against the forehead.

If the fitted member 31 were to extend up the vertical edge of the lens 17 of the right area 19, an enclosed volume surrounding the eyes results. The integrity of the enclosed volume is not as complete as would be the case for a full goggle set, but air movement, and thus movement of debris in the air stream is restricted.

Figure 1:
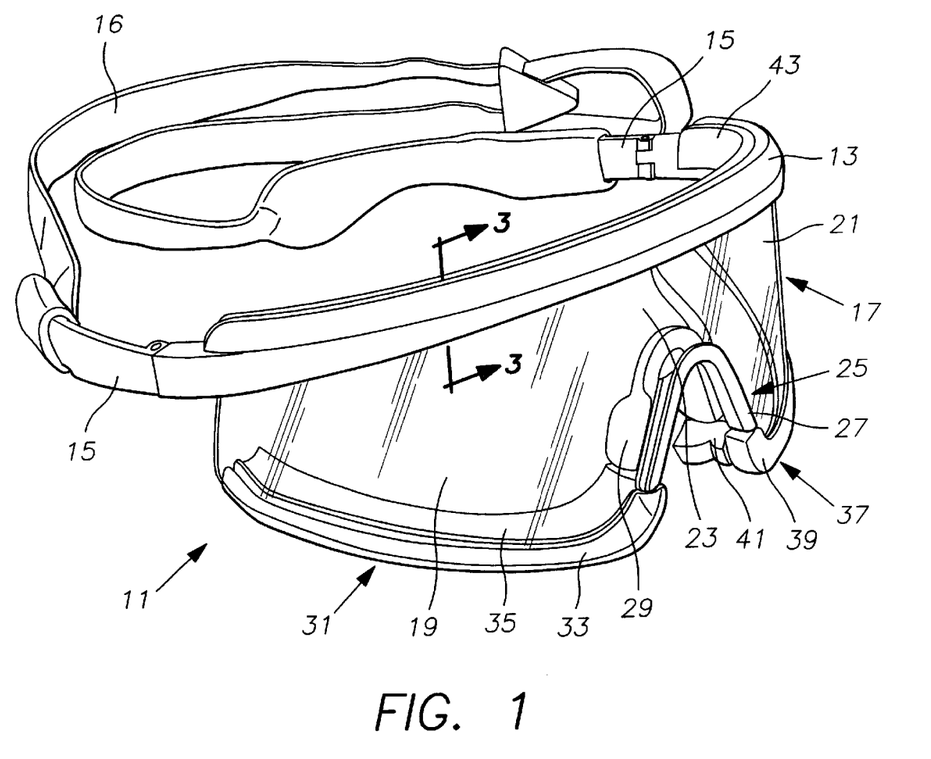
FIG. 1 is an illustration of a perspective view of the eye wear of the present invention and illustrating the fitted member attached as two pieces to the lower edge of a single lens and up to each side of the nose support structure.

In the configuration of FIG. 1, the engagement piece 33 will typically be purchased as a pre-fit to conform to right areas 19 having a generalized bottom edge configuration as shown in FIG. 1. It is possible that the engagement piece 33 could fit a number of configurations which are different, but which do not extremely deviate from the general shape seen in FIG. 1, or a similar general shape.

As can also be seen in FIG. 1, the sealing structure 35 extends up to and may have sealing contact with the rearwardly extending nose bridge engagement portion 29. The sealing structure 35 may thereby extend beyond the extent of the end of the fitted engagement piece 33 as it approaches the nose bridge support 25. The fitted engagement piece 33 may also abut the nose bridge support 25 and particularly the forward lens engaging portion 27.

Figure 2:
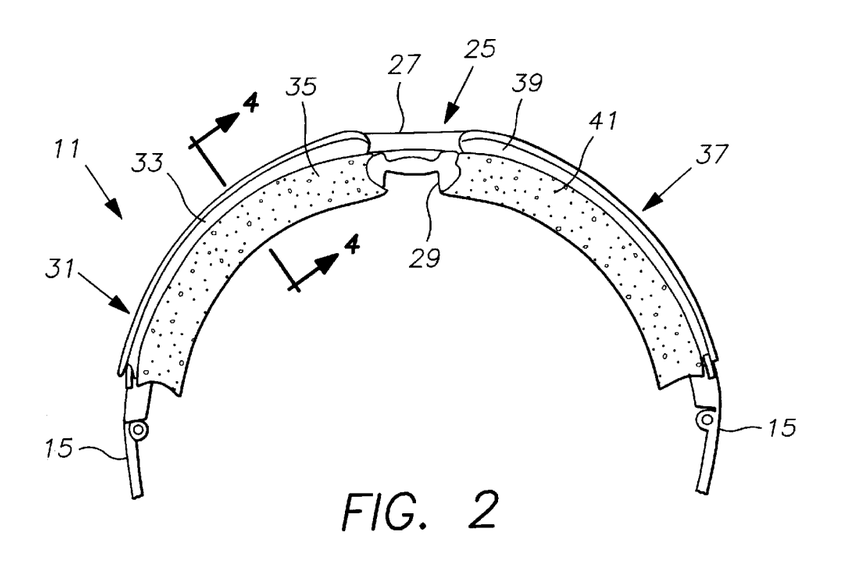
FIG. 2 is a bottom view of the eye wear of FIG. 1 and illustrating the prominence from a vertical angle of the sealing structure supported by the fitted members.

Referring to FIG. 2, a bottom view of the eye wear 11 of FIG. 1 illustrates the rearward extent of the sealing structures 35 and 41. A more complete view of the relationship of the forward lens engaging portion 27 and rearwardly extending nose bridge engagement portion 29 of the nose bridge support 25 is seen.

Figure 3:
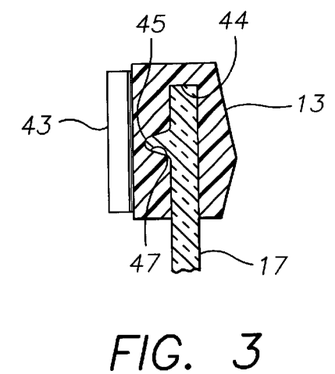
FIG. 3 is a view taken along line 3—3 of FIG. 1 and illustrating the manner in which the lens is held within the frame with a projection extending perpendicular to the general planar surface of the lens.

Referring to FIG. 3, an expanded view taken along line 3—3 of FIG. 1 is illustrated. The frontal support 13 has a slot 44 into which the lens 17 fits. The lens 17 has a rearward protrusion member 45 which rises significantly away from the planar extent of lens 17 and which interfits with a matching void 47 and both of which operate to keep the lens 17 secure within the curved frontal support 13. The overall shape of the member 45 may be round, square or triangular in both side and surface profile, and further configurations will be shown. The frontal support 13 is seen as having a downwardly directed slot 44, indicated by a lead line to the closed end of the slot, into which lens 17 fits.

Figure 4:
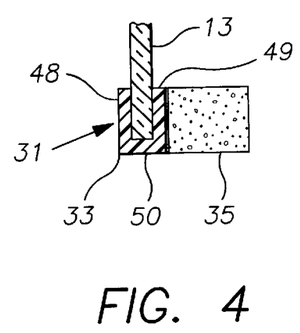
FIG. 4 is a sectional view taken through a fitted member shown in FIG. 2 and illustrating the press fit member supporting the sealing member.

Referring to FIG. 4, a generalized view of the fitted engagement piece 33 and attached sealing structure 35 is seen. The sealing structure 35 may be relatively long, both to give an adequate reach to the portion of the user's face being engaged, and to provide a softer fit by providing additional material for compression. The vertical depth of the material of the sealing structure 35 is sufficient to prevent any sagging or undue bending in a vertical direction. The fitted engagement piece 33 is seen as having a front wall 48 and a rear wall 49 both supported by a base member 50.

Figure 5:
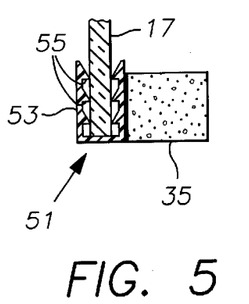
FIG. 5 is a variation on the fitted member of FIG. 4 and having a series of inwardly disposed engagement members.

Referring to FIG. 5, a variation on the design of the fitted engagement piece 33 of FIG. 4 is shown as a fitted engagement member 51 having a fitted engagement piece 53 having internally disposed gripping members 55. Gripping members help to provide greater holding force by making it easier to mount the engagement piece 53 onto the lens 17 than the force required to remove it.

Figure 6:
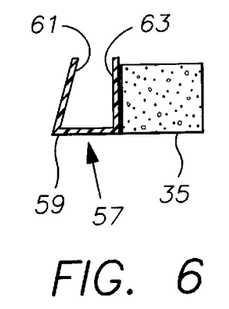
FIG. 6 is a variation on the fitted member of FIGS. 4 and 5 which is extruded and pre-stressed to better engage the lens.

Referring to FIG. 6, a variation on the design of the fitted engagement piece 33 of FIG. 4 is shown as a fitted engagement member 57 having a fitted engagement piece 59 having inwardly tilting preformed side walls 61 to assist in gripping the lower edge of the lens 17 (not shown in FIG. 6 in order to show the degree of pre stress on at least one of the side walls 61). The inwardly tilting front and rear walls 61 and 63 help to better distribute the bearing force of the side walls 61 on the lens 17 material to prevent a loosening of the side walls from becoming worn and flared thus preventing good fit of the engagement piece 33.

Figure 7:
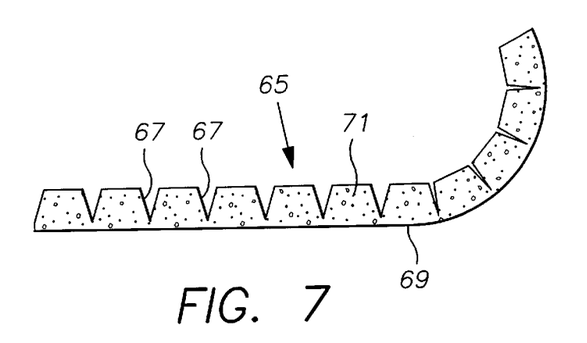
FIG. 7 is an example of a length of fitted material having a series of slots to enable easy conformance of the fitted material to the bottom edge of the lens and having any shape.

Referring to FIG. 7, a continuous length of fitted member 65 has a series of generally evenly spaced notches 67 in its fitted engagement piece 69. The notches 67 are formed in both the front and rear walls, although only a front wall 71 is visible from the vantage of FIG. 7. The sealing structure 35 extends away from the viewer of FIG. 7, and where the sealing structure 35 is of sufficient height, as will usually be the case, the notches 67 will also extend into its material. The notches 67 are of sufficient depth to enable any length of the engagement piece to bend sufficiently to closely engage the lower edge of the lens 13 at its smallest curvature. In some cases where the sharpest and most gentle curvature spacing is known, the notches 67 will have different depth or different angularity. Areas of slight curvature will have sharply angled notches while areas of sharp curvature will have large angled notches.

The fitted member 65 may be available in a continuous length to enable the user to cut a length to cover as much of the lower edge of a lens 17 as is desired. In addition to cutting the length to suit, the ends can be angle cut to enable the sealing structure 35 to extend beyond the end of the engagement piece 69, or to allow the engagement piece 69 to extend beyond the end of the sealing structure 35. In addition, the sealing structure 35 and the engagement piece 69 may be cut in other configurations as are necessary to more closely conform to and accommodate structures on the eye wear 11.

Figure 8:
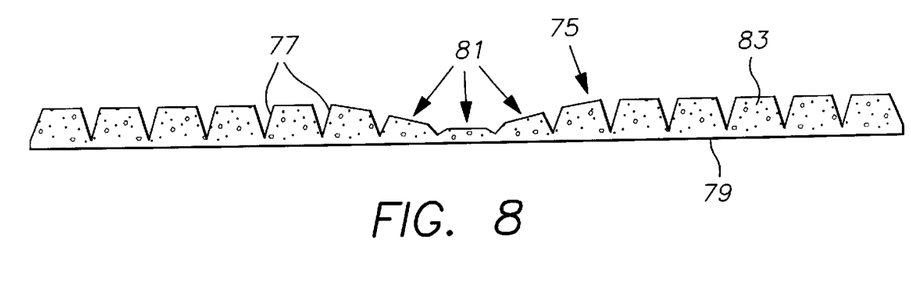
FIG. 8 is a continuous length of fitted material having a series of slots and cut in the middle to facilitate interfitting with a lens of an eye wear structure and for forming the nose bridge portion below the lens.

Referring to FIG. 8, in some cases, an eye wear 11 structure may lack a nose bridge support 25. In this case, a fitted member 75 may be provided having notches 77 in an engagement piece 79 which also has a wide gently sloping notch 81 removed from both a front wall 83 and a rear wall (not shown) and associated portions of the sealing structure (also not shown). The gently sloping notch 81 or curved removal of material from the fitted member 75 will prevent visual obstruction near the nose area 23. Otherwise, the individual portions between the notches 77 would fan out about the upper curvature of the bottom edge of lens 17 in the vicinity of the upper end of the nose bridge support 25, causing the visual obstruction.

As was the case for fitted member 65, the fitted member 75 can be manufactured with a central gently sloping notch 81, and overly long lengths to either side of the notch 81. The user can position the notch 81 at the nose area 23, begin fitting the lengths adjacent to the notch 81 and then trim the outer ends of the fitted member 75 to fit the outermost edges of the lens 17 as are needed.

Figure 9:
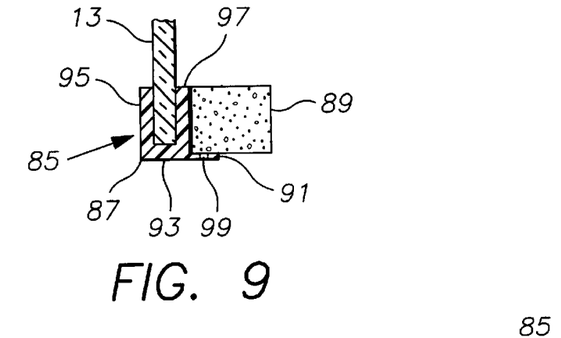
FIG. 9 illustrates a variation in the shape of the fitted member of FIG. 4 in which includes a small ledge for support of the sealing member.

Referring to FIG. 9, a modification of the fitted member 31 is seen as a fitted member 85 having a fitted engagement piece 87 and a sealing structure 89 which may have a slightly shorter depth to accommodate a ledge member 91. The ledge member 91 is parallel to a base member 93 which supports a front wall 95 and a rear wall 97. The ledge member 91 provides partial support for the sealing structure 89 and carries a series of drainage/ventilation slots 99 to help eliminate any moisture build up within the eye wear 11, and which moisture may be in gaseous or liquid form. If the sealing structure 89 is sufficiently porus to air, the moisture in the air may exit through both the slots 99 and any other surface of the sealing structure 89 exposed externally. In the case of liquid droplets which may move down the inside of the lens 13, the slots 99 provide an exit at a point closest to the rear of the rear wall 97, for the liquid to escape.

Figure 10:
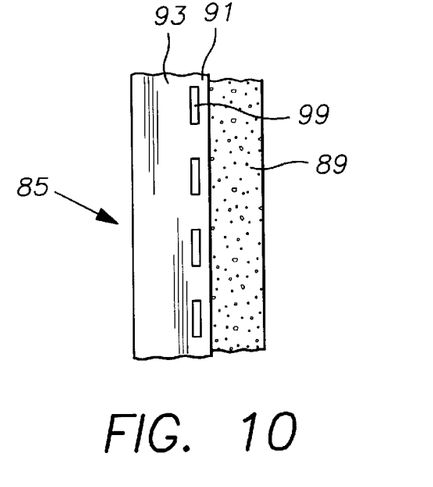
FIG. 10 is a bottom view of the fitted combination of FIG. 9 and illustrating a series of drainage slots formed in the small ledge.
Figure 11:
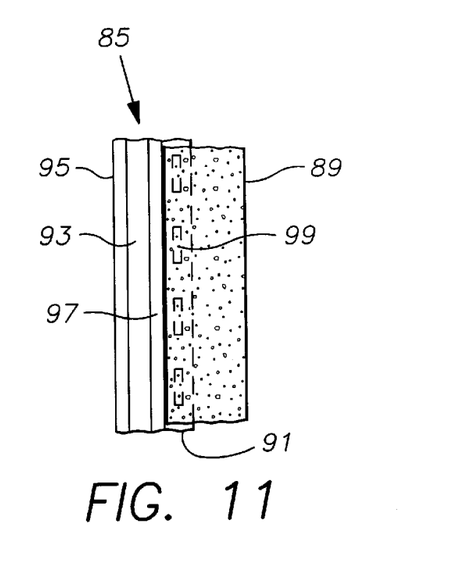
FIG. 11 is a top view of the fitted combination of FIG. 10 and illustrating a series of drainage slots formed in the small ledge in phantom.

FIG. 10 is a bottom view of the fitted member 85 and illustrating the regularity of spacing of the slots 99, and the extent to which the sealing structure 89 extends beyond the edge of the ledge 91. FIG. 11 is a top view of the fitted member 85 and showing the relationship of the front wall 95, rear wall 97 and base member 93. Also seen is the extent to which the sealing structure 89 both overhangs and is supported by the ledge 91.

Figure 12:
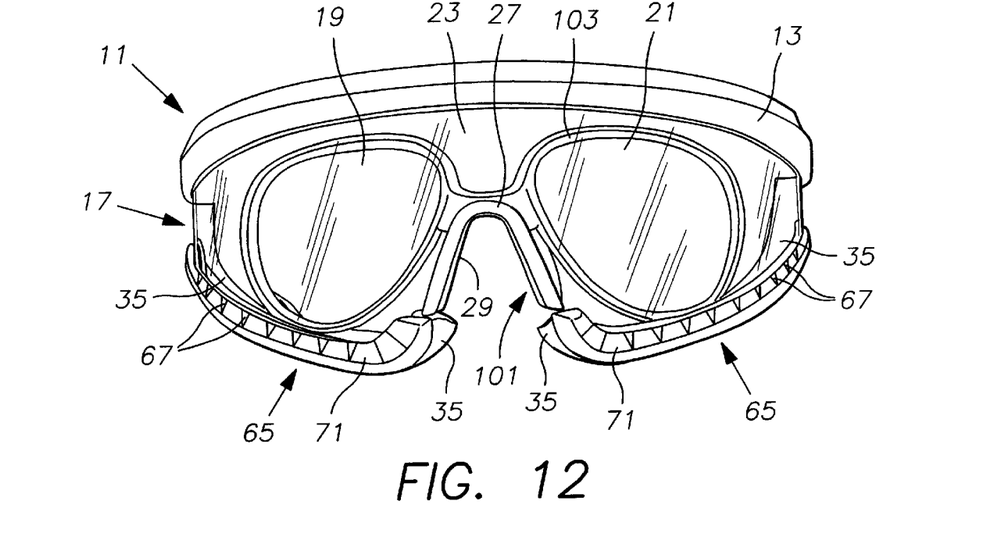
FIG. 12 illustrates a front view of an eye wear structure utilizing the fitted member of FIG. 7.

Referring to FIG. 12, the eye wear 11 is shown where the nose bridge support 25 is replaced by a nose bridge support 101 having an eyeglass frame 103 supported by the rearwardly extending nose bridge engagement portion 29. With the combination shown in FIG. 12, the eye wear 11 provides an expanded view, double protection for the eyes and yet has a goggle-type enclosure. Also seen are the fitted members 71 of FIG. 7 and the eye wear 11 is seen from a frontal angle of view. The continuousness the sealing structure 35 with respect to the rearwardly extending nose bridge engagement portion 29 is also seen. The sealing structure 35 can be seen through the lens 17 as rising all the way up to the level of the curved frontal support 13.

Figure 13:
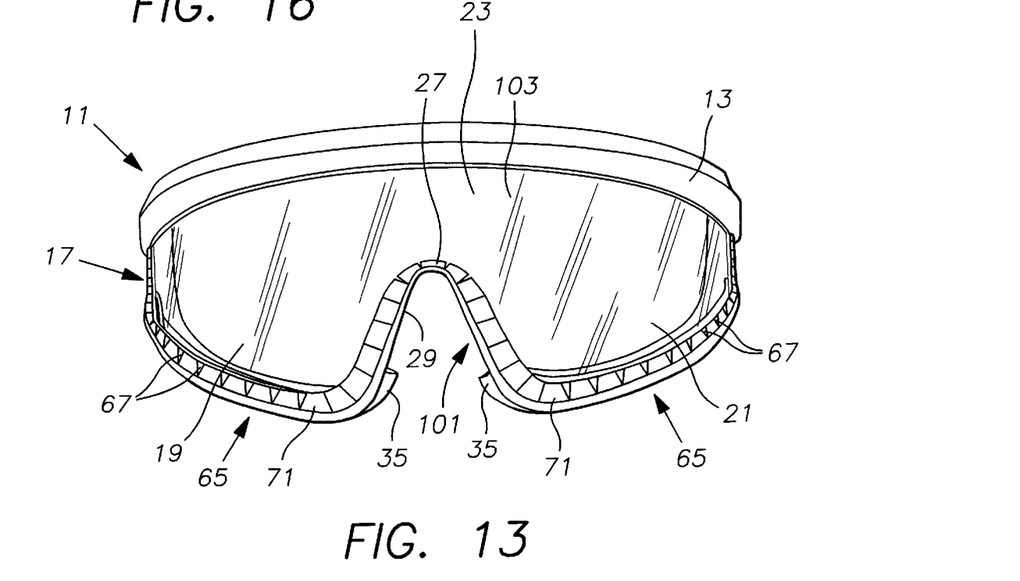
FIG. 13 illustrates a front view of an eye wear structure utilizing the fitted member of FIG. 8.

Referring to FIG. 13, the eye wear 11 is shown where the nose bridge support 25 and eyeglass frame 103 is absent and where the fitted member 75 of FIG. 8 is shown extending completely around the edges of the lens 17 which are not engaged by the slot 44 of the frontal support 13. The fitted member 65 extends downward from the frontal support and takes a sharp curve naturally before extending toward the center of the eye wear 11 underneath right area 19, curving upward again and also taking advantage of the notches 77 and up to that point having always curved in a direction compressing the space occupied by the notches 77. At the bottom of the nose area 23, the fitted member 65 curves in the opposite direction as it goes over an area which will fit over the bridge of the nose. Here the wide gently sloping notch 81 comes into use by preventing the portions of the fitted member 75 between the notches 77 from flaring widely at the base of the nose area 23. This prevents obstruction of vision. The sealing member 35 is seen through the lens 17 and illustrated is the sealing member 35's extension up to the level of the curved frontal support 13. A portion of the sealing member 35 can be seen at the front center of the eye wear 11 and below the nose area. The sealing member 35 thus acts not only to seal the eye wear 11 against a wearer's face, but also to cushion the eye wear 11 against the bridge of the wearer's nose.

Figure 14:
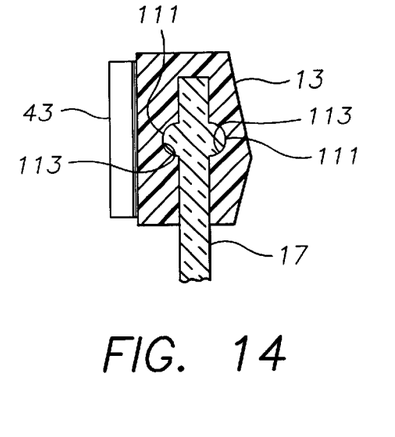
FIG. 14 shows an alternative method of engagement of the frontal support as was shown in FIG. 3, with the lens by using one or two oppositely disposed hemispherical protrusion members.

Referring to FIG. 14, a sectional view also taken along line 3—3 of FIG. 1 illustrates a variation on the rearward protrusion member 45 as a forward extending and rearward extending hemispherical protrusion member 111. It is hemispherical, with the radius lying on the general plane of the surface of the lens 19. The protrusion member 111 can be either in the forward position, rearward position or both. The illustration of FIG. 14 shows both forward and rearward structures for completeness. Each of the members 111 shown fit within a matching shaped hemispherical void 113 which lies off to one side of the slot 44 of the frontal support 13.

Figure 15:
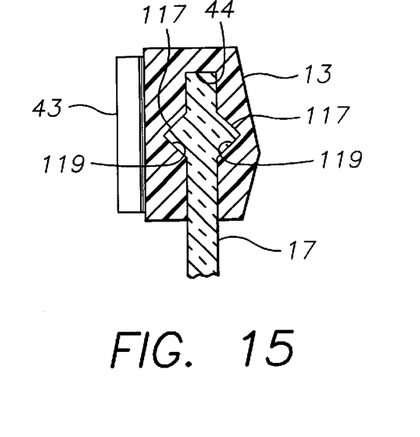
FIG. 15 shows an alternative method of engagement of the frontal support as in FIG. 14, where the protrusion members have an equilateral triangular shape.

Referring to FIG. 15, a sectional view also taken along line 3—3 of FIG. 1 illustrates a variation in shape of the forward extending and rearward extending hemispherical protrusion member 111, as a forward and rearward extending equilateral triangular protrusion member 117. The base of the triangular protrusion member 117 is about the same dimension as its two sides. The protrusion member 117 can also be either in the forward position, rearward position or both and is shown as both for illustration. Each of the members 117 shown fit within a matching shaped equilateral triangular void 119 which lies off to one side of the slot 44 of the frontal support 13.

Figure 16:
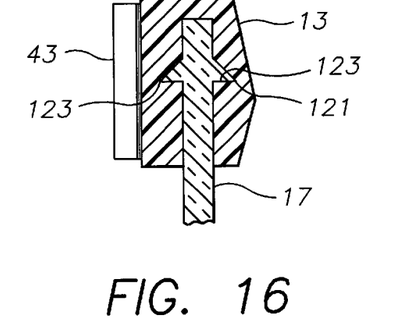
FIG. 16 shows an alternative method of engagement of the frontal support as in FIG. 15, where the protrusion members have a right triangular shape and are oriented to lock and capture the lens withing the frontal support in one direction.

Referring to FIG. 16, a sectional view also taken along line 3—3 of FIG. 1 illustrates a variation on the rearward protrusion member 45 as a forward extending and rearward extending right triangular member 121. The right triangular member 121 is oriented to facilitate the introduction of the lens 17 into the slot 44 and for a matching void 123 to capture the triangular member 121 within the void 123 to, in a less reversible way, capture the lens 17 within the slot 44. Depending upon the materials used, the difficulty in removing the lens 17 from the slot 44 will vary. The use of the member 121 will permit a lesser size member 121 to be used to give the same holding strength as another structure with a more reversible shape.

Figure 17:
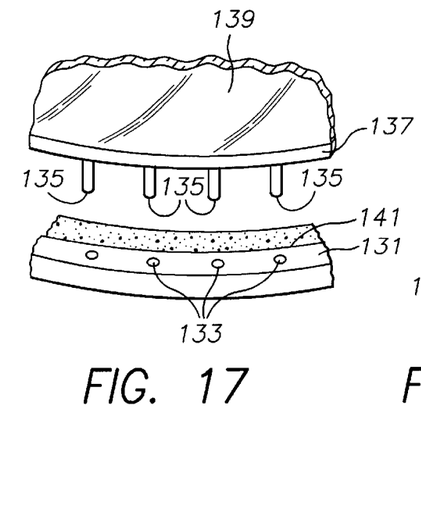
FIG. 17 is a perspective view of a bottom fitting protrusion member having a series of bores for interfitting with a series of downwardly extending pegs from the bottom surface of a lens or lens support and illustrating a rearwardly extending foam sealing member.

Beginning with FIG. 17, a further series variant structures for the invention are shown to illustrate the wide variety of structures and attachments which enable a sealing member to be secured relatively to a lens, such as lens 17, or a lens support structure surrounding an individually supported lens as is typically found in conventional eye wear. FIG. 17 is a perspective view of a bottom fitting protrusion member 131 having a series of bores 133 for interfitting with a series of downwardly extending pegs 135 from the bottom surface 137 of a lens 139. A rearwardly extending foam sealing member 141 is also seen. The pegs 135 fit into the bores 133 for a secure fit.

Figure 18:
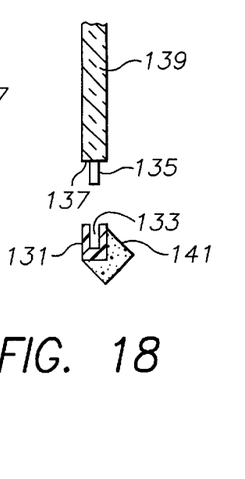
FIG. 18 is a side sectional view of the structure in FIG. 17, and illustrating the protrusion member's blind bores and which is attached to the bottom and rear surfaces of a bottom fitting protrusion member and having a main sealing surface at an angle to both bottom and rear surfaces.

FIG. 18 is a side sectional view of the structure in FIG. 17, where protrusion member 131 blind bores 133 are shown in section. However, FIG. 18 shows a variation as a sealing member 145 which is mounted at an approximate 45° angle and in which a sealing member 141 has an upper surface for engaging a bottom of the protrusion member 131, as well as forward surface for engaging a rear of the protrusion member 131.

Figure 19:
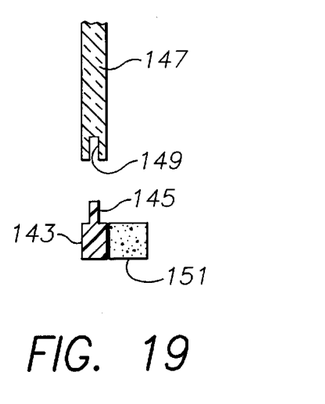
FIG. 19 is a side sectional view of a variant of the structure of FIGS. 17 and 18, but where the protrusion member supports the series of pegs seen in FIGS. 18 and 17 and where the bottom surface of a lens or lens support includes a series of interfitting blind bores.

FIG. 19 is a side sectional view of a variant of the structure of FIGS. 17 and 18, but where a protrusion member 143 supports a series of pegs 146 and where the bottom surface of a lens 147 includes a series of blind bores 149 and where a sealing member 151 extends rearwardly of the protrusion member 143.

Figure 20:
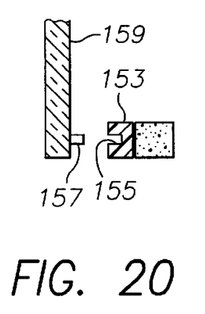
FIG. 20 is a side sectional view of a rearwardly fitting protrusion member having a series of forwardly directed bores for interfitting with a series of rearwardly extending pegs from the rearward surface of a lens or lens support and illustrating a rearwardly extending foam sealing member.

Referring to FIG. 20, a side sectional view of a rearwardly fitting protrusion member 153 having a series of forwardly directed bores 155 for interfitting with a series of rearwardly extending pegs 157 from the rearward surface of a lens 159. Affixation in any of the pegs, including pegs 157 into the bores, including bores 155 may be augmented by friction interference shape interaction, adhesive or glue or a snapping interfitting action.

Figure 21:
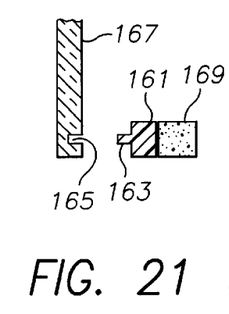
FIG. 21 is a side sectional view of a rearwardly fitting protrusion member having a series of forwardly directed pegs for interfitting with a series of rearwardly extending bores from the rearward surface of a lens or lens support and illustrating a rearwardly extending foam sealing member.

Referring to FIG. 21, a side sectional view of a rearwardly fitting protrusion member 161 having a series of forwardly directed pegs 163 for interfitting with a series of rearwardly extending bores 165 from the rearward surface of a lens 167, is seen. Also seen is a rearwardly extending foam sealing member 169 having a rectangular profile.

Figure 22:
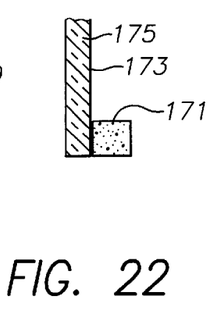
FIG. 22 is a side sectional view of a rearwardly fitting foam sealing member attached to the rearward surface of a lens or lens support utilizing at least one of glue, static plastic member or adhesive.

Referring to FIG. 22, is a side sectional view of a rearwardly fitting sealing member 171 attached to the rearward surface 173 of a lens 175 utilizes at least one of glue, static plastic member or adhesive.

Figure 23:
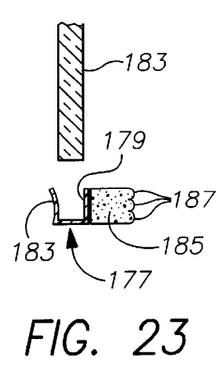
FIG. 23 is a side sectional view of a bottom fitting protrusion member in the shape of a channel having a "U" cross sectional shape upwardly disposed to fit around the bottom portion of a lens or lens support and illustrating a rearwardly extending foam sealing member with a ribbed surface to insure greater sealing.
Figure 24:
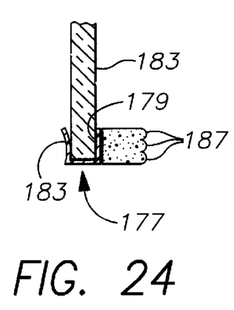
FIG. 24 is a side sectional view of a bottom fitting protrusion member as seen in FIG. 23 and shown in position on the bottom portion of a lens or lens support.

Referring to FIG. 23, a side sectional view of a bottom fitting protrusion member 177 is in the shape of a channel having a "U" cross sectional shape and has a rear wall which is opposite forward curved wall 181, the curvature to facilitate the upwardly disposed fitting onto a lens 183. A rearwardly extending foam sealing member 185 with a ribbed surface 187 to insure greater sealing. FIG. 24 is a side sectional view of the bottom fitting protrusion member 177 as seen in FIG. 23 and shown in position on the bottom portion of lens 183.

Figure 25:
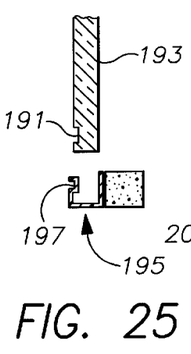
FIG. 25 is a variation on the side sectional view seen in FIG. 24 and in which at least a portion of a channel in the lower forward portion of a lens or lens support is engaged by one side of a clip-shaped or "U" shaped channel member having an extension of one side of the channel member into the channel to form a positive lock.

FIG. 25 is a variation on the side sectional view seen in FIG. 24 and in which at least a portion of a forwardly "U" shaped channel 191 is cut in a lower forward portion of a lens 193. A clip-shaped or "U" shaped channel protrusion member 195 has an extension of one side 197 of the protrusion member 195 into the channel 191 of the lens 193 to form a positive lock. When the protrusion member 195 is not in place with respect to the lens 193, an attractive channel 191 is seen. The depth, shape and detail relief of the channel 191 may be varied for decorative effect.

Figure 26:
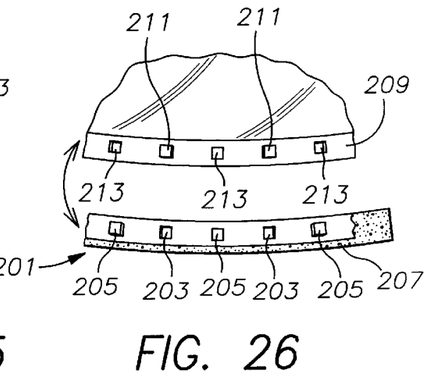
FIG. 26 is a perspective view of separated members of a rearward fitting protrusion member having a an alternating series of rectangular extensions and rectangular depressions, and having a rearwardly extending sealing member, and shown opposite the bottom rear surface of a lens or lens support and having a complementary alternating series of rectangular extensions and rectangular depressions, for interfitting with the rectangular extensions and rectangular depressions of the protrusion member for an interlocking fit.

Referring to FIG. 26, a perspective view of a separated rearward fitting protrusion member 201 having a an alternating series of raised extensions 203 and depressions 205, and having a rearwardly extending sealing member 207, and shown opposite the bottom rear surface 209 of a lens support and having a complementary alternating series of raised extensions 211 and depressions 213, for interfitting with the raised extensions 203 and depressions 205 of the protrusion member 201 for an interlocking fit. The extensions 203 and 211 can be made enlarged for a friction or snap fit with respect to the rectangular depressions 205 or 213.

Figure 27:
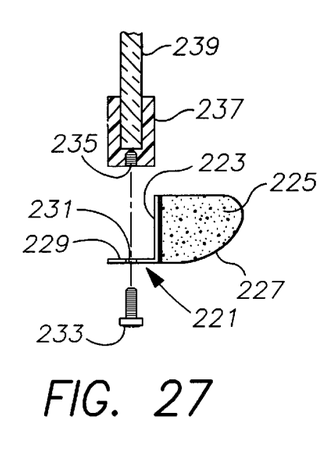
FIG. 27 illustrates a side sectional view of a bottom fitting protrusion member having a general "L" shape and including a vertical member from which a rearwardly extending and shaped sealing member extends having a more gently sloping lower side, and a horizontal member having an aperture for engagement with a threaded member extending through to a threaded bore into the bottom surface of a lens or lens support to secure the protrusion member to the lens or lens support.

Referring to FIG. 27, a side sectional view of a bottom fitting protrusion member 221 having a general "L" shape and including a vertical member 223 from which a rearwardly extending and shaped sealing member 225 extends having a more gently sloping lower side 227, and a horizontal member 229 having an aperture 231 for engagement with a threaded member 233 extending through to a threaded bore 235 into the bottom surface of a lens support 237 surrounding a lens 239. The threaded members 233 are expected to be small, about the same size as the threaded members used for eye wear hinges. The lower curved surface 227 of the sealing member 225 provides a surface which matches more nearly with the face of the user as the sealing member 225 undergoes some upward deformation to build the slight force which aids sealing.

Figure 28:
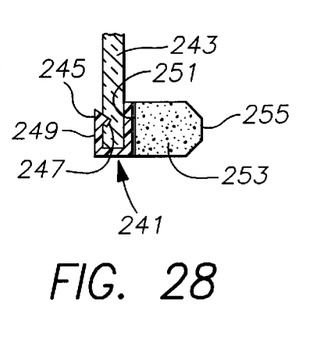
FIG. 28 is a side sectional view similar to that seen in FIG. and in which at least a portion of a channel in the lower forward portion of a lens or lens support is engaged by a laterally hook shaped structure extending from the top and one side of a clip-shaped or "U" shaped channel member having a sloping upper portion leading to an extension rib for facilitating the engagement of the channel shaped protrusion member from the lower portion of a lens or lens support.

Referring to FIG. 28 a side sectional view similar to that seen in FIG. 25 and in which at least a portion of a somewhat "U" shaped and hook shaped and channeled protrusion member 241 is attached at the lower portion of a lens 243. The lens 243 also carries a small groove 245 which is engaged by a hook shaped cross sectional upper portion 247 of a front wall 249. The upper continuous slope of the upper portion 247 aids in snapping the protrusion member 241 in place. A rear wall 251 of the protrusion member 241 is attached with a rearwardly extending sealing member 253 having a hemi-octagonal rear surface 255 including a top surface, upper 45° angled surface, rear surface lower 45° angled surface and lower surface, the upper and lower surfaces extending back to the rear wall 251.

Figure 29:
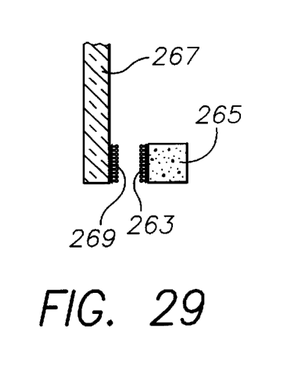
FIG. 29 is a side sectional view of a rearwardly fitting protrusion member having one of hook and loop members attached to a forward surface thereof and a rearward surface of a lens or lens support having the other one of hook and loop members to engage the protrusion member to the lens or lens support.

Referring to FIGS. 29, a side sectional view of a rearwardly fitting protrusion member 261 having or even merely consisting of one of hook and loop members 263 attached to a forward surface of a protrusion member or directly to a sealing member 265 and a rearward surface of a lens 267 the other one of hook and loop members 269 to engage the one of hook and loop members 263.

Figure 30:
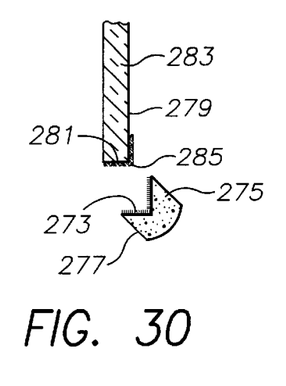
FIG. 30 is a side sectional view of a rearwardly and downwardly fitting "L" shaped protrusion member having one of hook and loop members attached to a forward and upward surface thereof and shown with respect to a rearward and downward surface of a lens or lens support having the other one of hook and loop members to engage both the forward and upward surface of the protrusion member to the lens or lens support, and a rearwardly and downwardly extending sealing member having a terminal curved surface.

FIG. 30 is a side sectional view of a rearwardly and downwardly fitting "L" shaped protrusion member 271 having one of hook and loop members 273 attached to a forward 275 and upward 277 surface thereof and shown with respect to a rearward surface 279 and a downward surface 281 of a lens 283 having the other one of hook and loop members 285 to engage both the forward and upward surface of the one of hook and loop members 273.

Figure 31:
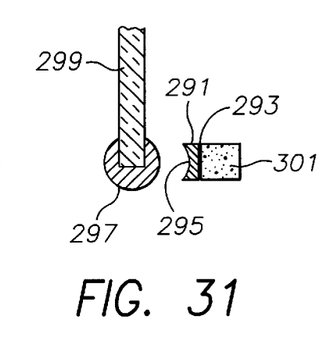
FIG. 31 is a side sectional view of a rearwardly fitting magnetic protrusion member having a rearward flat side and a curved front opposite side for attachment to a magnetic or metallic curved lower portion of a lens support having a curved surface complementary to the curved front of the magnetic protrusion member and including a rearwardly extending rectangular cross shaped sealing member.

FIG. 31 is a side sectional view of a rearwardly fitting magnetic protrusion member 291 having a rearward flat side 293 and a curved front opposite side 295 for attachment to a curved lower portion of a metallic lens support 297 supporting lens 299 having a curved surface complementary to the curved front of the protrusion member 291 and including a rearwardly extending rectangular sealing member 301.

Figure 32:
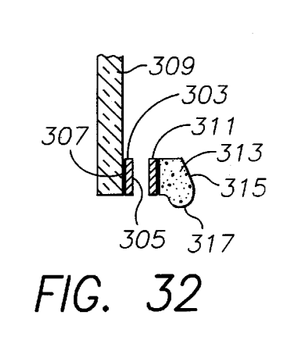
FIG. 32 is a side sectional view of a rearwardly fitting magnetic lens support member having a rearward side and forward side attached to a lens by glue, bonding or any other method, and a magnetic protrusion member having a magnetic characteristic of complementary polarity to the magnetic lens support member.

Referring to FIG. 32, a side sectional view of a rearwardly fitting magnetic lens support member 303 having a rearward side 305 and forward side 307. The magnetic lens support member 303 is shown attached to a lens 309 by glue, bonding or any other method. A magnetic protrusion member has a magnetic characteristic of complementary polarity to the magnetic lens support member 303, and is attached to a rearwardly extending downwardly curving sealing member 313. A downwardly and rearwardly sloping surface 315 transitions into a downwardly curved surface 317 to provide a supported sealing with a face of the user.

Figure 33:
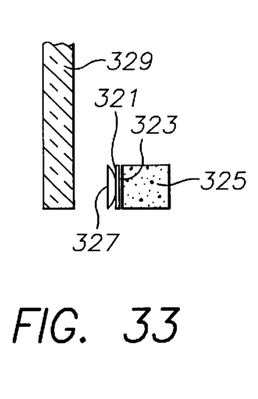
FIG. 33 is a side sectional view of a rearwardly fitting suction cupped protrusion member having a rearward surface and a forward suction cup for attachment to a curved lower portion of a lens or lens support and including a rearwardly extending rectangular sealing member.

Referring to FIG. 33 is a side sectional view of a rearwardly fitting suction cupped protrusion member 321 having a rearward flat surface 323 for attachment to a rectangular cross sectional shaped sealing member 325. A frontal suction cup 327 is seen opposing a lens 329.

Figure 34:
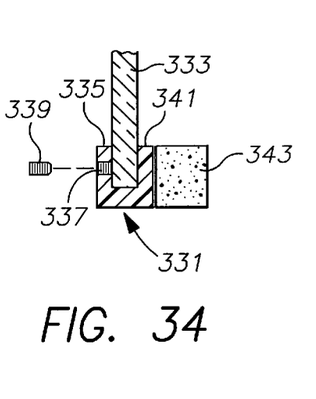
FIG. 34 is a side sectional view of a "U" shaped channel protrusion member engaging the bottom of a lens or lens support with a forward side of the channel having a forward threaded bore engaged by a set screw and a rearward side of the channel having a rearwardly extending rectangular sealing member.

FIG. 34 is a side sectional view of a "U" shaped channel protrusion member 331 engaging the bottom of a lens 333 with a forward side 335 of the channel protrusion member 331 having a forward threaded bore 337 engaged by a set screw 339 and a rearward side 341 of the channel protrusion member 331 having a rearwardly extending rectangular sealing member 343. The channel protrusion member 331 is held in place by the compressive and biting force of the set screw 339 against the lens 333.

Figure 35:
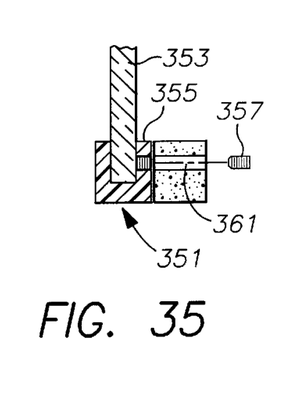
FIG. 35 is a side sectional view of a "U" shaped channel protrusion member engaging the bottom of a lens or lens support with a rearward side of the channel having a rearward threaded bore engaged by a set screw and a rearward side of the channel having a rearwardly extending rectangular sealing member having an access bore in alignment with the threaded bore for admission and insertion of the set screw.

FIG. 35 is a side sectional view of a "U" shaped channel protrusion member 351 engaging the bottom of a lens 353 with a rearward side 355 of the channel protrusion member 351 having a rearward threaded bore 357 engaged by a set screw 359. The rearward side of the channel protrusion member 351 also having a rearwardly extending rectangular sealing member 361 having an access bore 363 in alignment with the threaded bore 357 for admission and insertion of the set screw 359.

Figure 36:
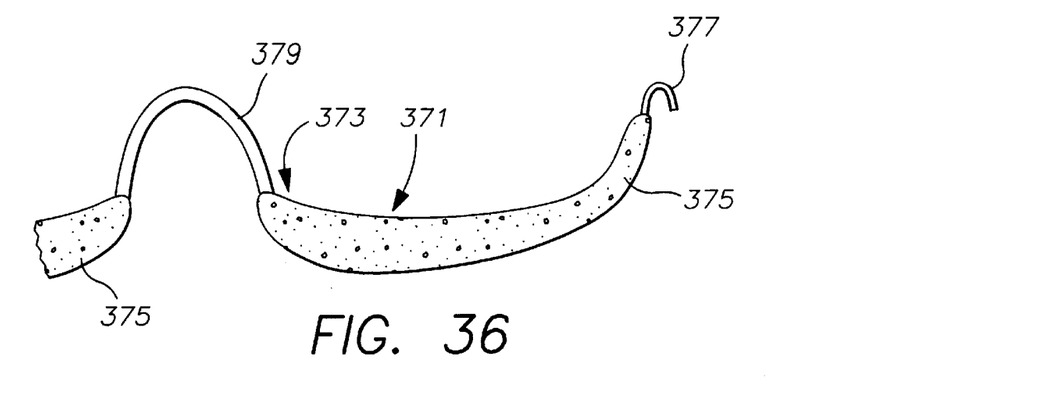
FIG. 36 is a rear view of the right two thirds of an extended protrusion member and sealing member having a structural protrusion portion including a suspension nose bridge and side hooks for engaging the forward temple members of eye wear, and an attached rearwardly extending sealing member of rounded shape supported by the portions of the protrusion member between the suspension nose bridge and side hooks.

FIG. 36 is a rear view of the right two thirds of an extended assembly 371 including a protrusion member 373 and sealing member 375. The left half of the member 371 is a mirror image of the shown right half. The protrusion member 373 extends from a hook end 377 and a suspension nose bridge 379 and then to an opposite hood end 377 (not shown). The assembly 371 is intended to be suspended between the two arms of the temple portions of eye wear, and also supported at the middle by the suspension nose bridge 379 either against the user's nose or against some other structure.

Figure 37:
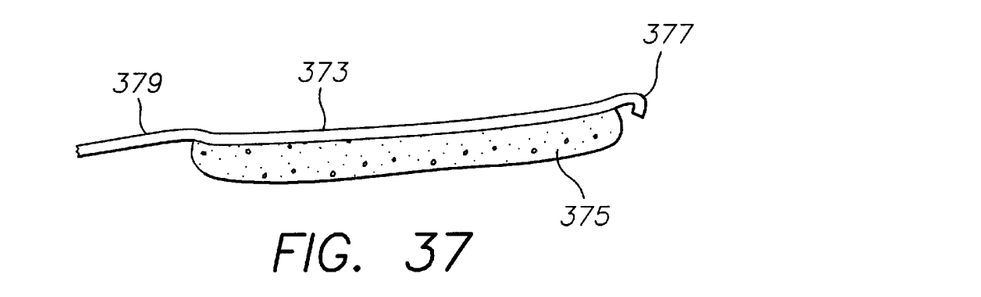
FIG. 37 is a downward view of the extended protrusion member of FIG. 36.
Figure 38:
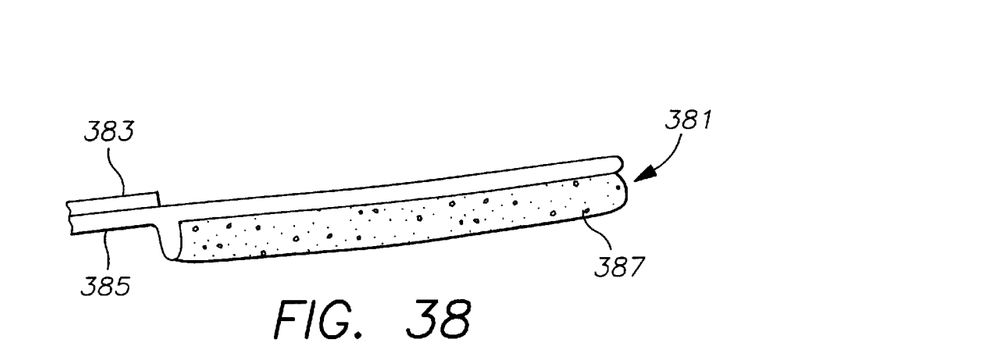
FIG. 38 is a top view of the right two thirds of an extended molded integral protrusion and sealing member having an integrally molded forward lens engaging portion 27 and a rearwardly extending nose bridge engagement portion integral with the protrusion member.

The attached rearwardly extending sealing member 375 can be of rounded shape and supported to any extent by the portions of the protrusion member 373, including having the sealing member 375 surround the protrusion member 373 and partially surround the protrusion member 373. Referring to FIG. 38, a downward view of the assembly 371 and extended protrusion member 373 of FIG. 37 is shown.

FIG. 39 is a top view of the right two thirds of an extended molded integral protrusion and sealing member 381 having an integrally molded forward lens engaging portion 383 and a rearwardly extending nose bridge engagement portion 385 integral with the molded integral protrusion and sealing member 381. The left half of the member 381 is a mirror image of the shown right half. The differing portions of the molded integral protrusion and sealing member 381 need not be of the same hardness, and reinforcement dipping and treatment is permissible to give a sealing portion 387 hardness different than the protrusion support portions.

Figure 39:
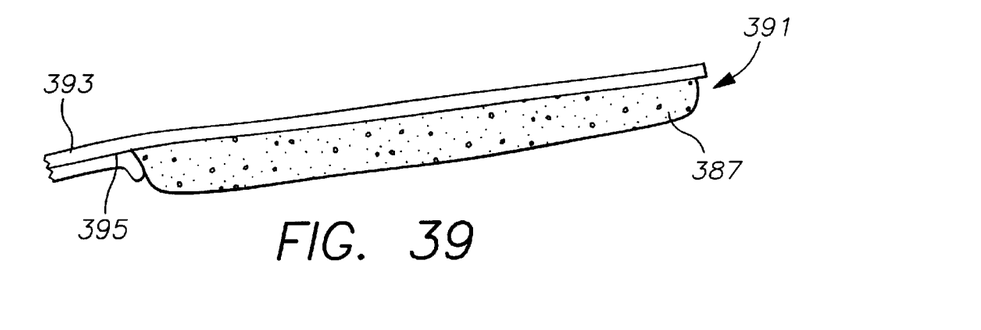
FIG. 39 is a top view of the right two thirds of an extended molded integral protrusion and sealing member having an integrally molded forward "U" shaped lens engaging portion and a rearwardly extending nose bridge engagement portion.

FIG. 39 is a top view of the right two thirds of an extended molded integral protrusion and sealing member 391 having an integrally molded forward "U" shaped lens engaging portion 393 and a rearwardly extending nose bridge engagement portion 395. The left half of the member 391 is a mirror image of the shown right half. A sealing portion 397 can be softer or harder than integrally molded forward "U" shaped lens engaging portion 393, and reinforcement dipping and treatment is permissible.

Figure 40:
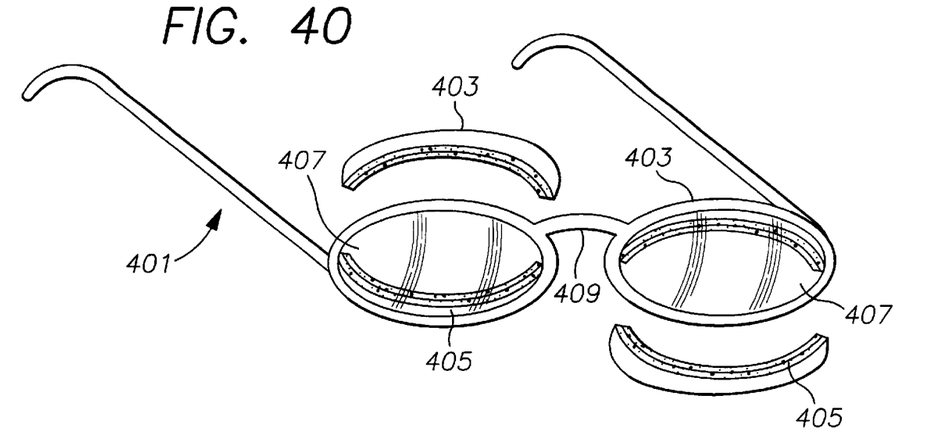
FIG. 40 is a perspective view of a set of conventional spectacles having single lens upper and lower engagement members immediatly above and below individual separated lens areas.

FIG. 40 is a perspective view of a set of conventional spectacles 401 having single lens structure upper and lower sealing members 403 and 405 immediately above and below an individual separated lens 407 structure. The sealing members 403 and 405 do not cross the center of a bridge structure 409.

Figure 41:
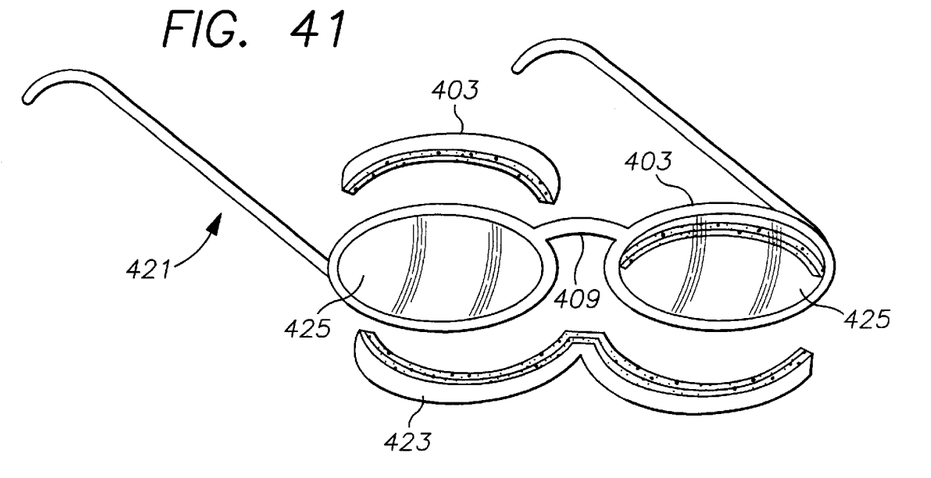
FIG. 41 illustrates a set of conventional spectacles utilizing a lower engagement member extending across both individual separated lens areas utilized in conjunction with a single lens upper engagement member.

FIG. 41 illustrates a set of conventional spectacles 421 utilizing a lower sealing member 423 extending across both individual separated lens areas 425 utilized in conjunction with individual single lens upper sealing members 403 as were seen in FIG. 40.

Figure 42:
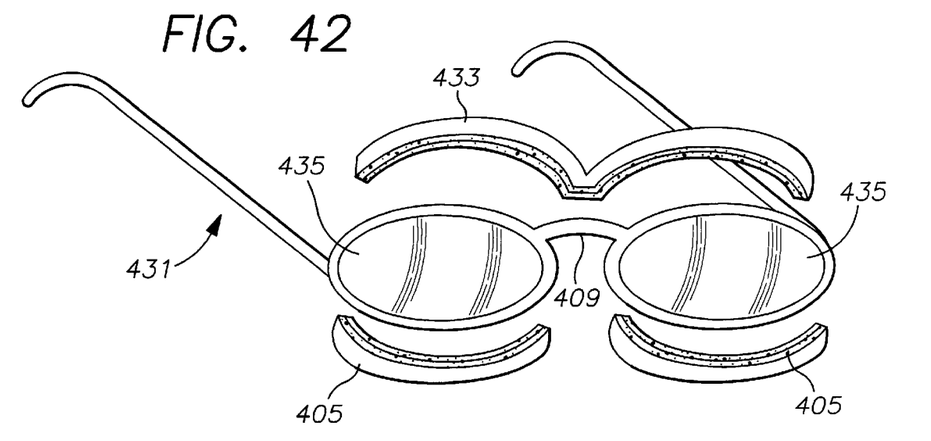
FIG. 42 illustrates a set of conventional spectacles utilizing an upper engagement member extending across both individual separated lens areas utilized in conjunction with a pair of single lens lower engagement members.

FIG. 42 illustrates a set of conventional spectacles 431 utilizing an upper sealing member 433 extending across both individual separated lens areas 435. The upper sealing member 433 is utilized in conjunction with a pair of single lens lower sealing members 405 as were seen in FIG. 40.

The present invention may be used in any setting in which an expanded lens eye wear structure is desired to be fitted with a removable enclosing structure to give goggle-like sealing protection for the user. Multiple variations on this invention are certainly possible, since variations can occur with any one or any combination of the components of several of the fitted structures, sealing structures, lens interfitting structures described in the eye wear invention. Modifications to all parts of the invention may occur to those skilled in the art, and those modifications may be produced without departing from the spirit and scope of the invention. Therefore, included within the patent warranted hereon are all such changes and modifications as may reasonably and properly be included within the scope of this contribution to the art.

What is claimed:

1. A fitted member for removable deployment onto pre-existing eye wear of known art which is incapable of selective sealing out of at least one of wind, debris, and foreign matter from the eyes of a user, said eye wear having a peripheral region corresponding to a user's facial region surrounding the user's two eyes comprising:

an engagement piece having a first side and a second side oppositely disposed with respect to said first side, and at least one engagement surface for user selectably removable attachment adjacent an edge of and for deriving support from said peripheral region of the eye wear in a manner requiring no modification of the eye wear and that enables easy removal of said engagement piece from the eye wear to enable selected use of said eye wear structure with and without said fitted member, and wherein said engagement piece has a base member supporting a front wall having said first side and a first internally disposed side and supporting a rear wall having said second side and a second internally disposed side, a sealing structure attached to said second side of said engagement piece and extending away from said second side for conforming to a designated portion of the user's facial region and to extend therefrom to said second side of said engagement piece for, in concert with said eye wear, selective sealing out of at least one of wind, debris, and foreign matter from the eyes of the user.

2. The fitted member recited in claim 1 wherein said front wall of said engagement piece is curved inwardly to facilitate a pinch fit attachment of said engagement piece adjacent said edge of said eye wear structure.

3. The fitted member recited in claim 1 wherein one of said front and rear wall of said engagement piece has a projection directed toward the other of said front and rear wall to engage said attachment member with respect to a groove carried adjacent an edge of said eye wear structure.

4. The fitted member for use with eye wear as recited in claim 1 and further comprising:

a first area of one of hook and loop members attached to said engagement piece, and a second area of the other of hook and loop members engageable with said first area and removably attachable adjacent said edge of said eye wear structure.

5. The fitted member for use with eye wear as recited in claim 1 wherein said engagement piece is magnetic and wherein said first side is shaped for complementary engagement to said edge of said eye wear structure.

6. The fitted member recited in claim 1 wherein at least one of said base member, said first side and said second side of said engagement piece carries a support ledge for partially supporting said sealing structure.

7. The fitted member recited in claim 6 wherein said ledge member carries a plurality of spaced apart slots to enable moisture to pass through.

8. The fitted member recited in claim 1 wherein at least one of said first and said second sides of said engagement piece has a series of spaced apart notches to enable said engagement piece to be fitted along different sizes of a radius of contour on said eye wear.

9. The fitted member recited in claim 1 wherein said sealing structure comprises a deformable structure easily deformable against a wearer's face to further facilitate blockage of said at least one of wind, debris, and foreign matter from entering between said sealing structure and said wearer's face.

10. The fitted member recited in claim 9 wherein said deformable structure is a foam piece having a porus volume and an open cell structure.

11. The fitted member recited in claim 10 wherein said foam piece has at least one surface which is impermeable.

12. The fitted member recited in claim 1 wherein at least one of said front and rear walls carries a threaded aperture and further composing a set screw carried within said aperture for providing force engagement with respect to an edge of said eye wear structure.

13. The fitted member for use with eye wear as recited in claim 1 wherein said engagement piece carries at least one of a plurality of pegs and blind bores and wherein said engagement piece is for engagement with an edge of an eye wear structure carrying the other of said plurality of pegs and blind bores to facilitate attachment of said engagement piece to said eye wear structure.

14. The fitted member for use with eye wear as recited in claim 1 wherein said engagement piece carries at least one of a first plurality of raised extensions and depressions and wherein said engagement piece is for engagement with a surface of an eye wear structure carrying a complementary second plurality of raised extensions and depressions to facilitate attachment of said engagement piece to said eye wear surface.

15. An eye wear structure comprising:
   a frontal support having a downwardly directed slot and a void opening into said slot at an angle with respect to said slot;
   a continuous lens having a curved planar surface having an upper edge fitted into said downwardly directed slot and carrying a protrusion member arising from the curved planar surface of said lens and complementary to and fittable within said void to hold said lens within said frontal support, said continuous lens having an edge;
   a fitted sealing member user selectably removably attached adjacent said edge for providing a barrier to at least one of wind, debris, and foreign matter from entering an eye area of a wearer of said eye wear structure.

16. The eye wear structure recited in claim 15 wherein said protrusion member has a hem-circular sectional profile and said void matches said hem-circular sectional profile.

17. The eye wear structure recited in claim 15 wherein said protrusion member has a right triangular sectional profile and said void matches said right triangular sectional profile.

18. The eye wear structure recited in claim 15 wherein said protrusion member has an equilateral triangular sectional profile and said void matches said equilateral triangular sectional profile.

19. The eye wear structure recited in claim 15 wherein said protrusion member is a first protrusion member and said continuous lens carries a second protrusion member, oppositely disposed with respect to said first protrusion member.

20. The eye wear structure recited in claim 15 and further comprising:
   an engagement piece having a first side and a second side oppositely disposed with respect to said first side, and at least one engagement surface for user selectably removable attachment adjacent said edge of said continuous lens;
   a sealing structure attached to said second side of said engagement piece and extending away from said second side for engaging the face of a wearer of said eye wear.

21. The eye wear structure recited in claim 20 wherein said engagement piece has a base member supporting a front wall having said first side and a first internally disposed side and supporting a rear wall having said second side and a second internally disposed side, and wherein said edge of said continuous lens abuts said base member.

22. The eye wear structure recited in claim 21 wherein at least one of said first and said second sides of said engagement piece has a series of spaced apart notches to enable said engagement piece to be fitted along different sizes of a radius of contour on said eye wear.

23. The eye wear structure recited in claim 22 wherein said engagement piece carries a gently sloping notch along the length of said engagement piece and wherein said continuous lens has a right area, a left area, and a nose area, and where said engagement piece extends continuously from said right area through said nose area and to said left area and where said gently sloping notch reduces visibility blockage adjacent said nose area.

24. An eye wear sealing system for removable deployment onto pre-existing eye wear of known art having a peripheral region corresponding to a wearer's facial region surrounding the wearer's two eyes; comprising:
   at least one resilient sealing member made and arranged to conform to a designated portion of the wearer's facial region and to extend therefrom to a corresponding designated portion of the peripheral region of the eye wear for selective sealing out of at least one of wind, debris and foreign matter from the eyes of the wearer, and
   attachment means for deploying said resilient sealing member onto the peripheral region of the eye wear in a manner that requires no modification of the eye wear and that enables easy removal of the sealing member from the eye wear wherein said attachment means further comprises:
   an engagement piece having a cross-section configured as a generally U-shaped channel having a floor and two walls, made and arranged to frictionally engage the designated portion of the peripheral region of the eye wear within the channel with a wall surface facing the user, said resilient sealing member being permanently attached to the wall surface facing the user; and
   a support flange configured in said engagement piece extending from the floor of the channel to a predetermined extent past the wall surface facing the user, permanently attached to and providing support for a corresponding surface portion of said sealing member.

* * * * *